United States Patent [19]

Young et al.

[11] Patent Number: 4,728,466

[45] Date of Patent: Mar. 1, 1988

[54] PROCESS FOR THE PRODUCTION OF ALIPHATIC PHOSPHONIC ACIDS

[75] Inventors: Kai W. Young, Cary, N.C.; John J. Zullo, Flemington, N.J.

[73] Assignee: Rhone-Poulenc Nederland B.V., Amsteiveen, Netherlands

[21] Appl. No.: 54,381

[22] Filed: May 26, 1987

Related U.S. Application Data

[63] Continuation of Ser. No. 789,025, Oct. 18, 1985, abandoned.

[51] Int. Cl.$^4$ ............................................. C07F 9/38
[52] U.S. Cl. ............................................. 260/502.4 R
[58] Field of Search ................................. 260/502.46

[56] References Cited

U.S. PATENT DOCUMENTS

| | | | |
|---|---|---|---|
| 3,626,037 | 12/1971 | Randall et al. | 260/502.4 G |
| 3,699,195 | 10/1972 | Randall et al. | 260/502.4 G |
| 3,728,381 | 4/1973 | Randall et al. | 260/502.4 G |
| 3,787,486 | 1/1974 | Randall et al. | 260/502.4 G |
| 3,808,265 | 4/1974 | Randall et al. | 260/502.4 G |
| 3,833,645 | 9/1974 | Theobald et al. | 260/502.4 G |
| 3,896,163 | 7/1975 | Jacques | 260/502.4 G |
| 4,018,819 | 4/1977 | Rohn et al. | 260/502.4 G |
| 4,064,163 | 12/1977 | Drach et al. | 260/502.4 G |
| 4,293,505 | 10/1981 | Randall | 260/502.4 G |
| 4,322,371 | 3/1982 | Stabler | 260/502.4 G |

FOREIGN PATENT DOCUMENTS 2148549  4/1973  Fed. Rep. of Germany ... 260/502.4 G

*Primary Examiner*—J. E. Evans
*Attorney, Agent, or Firm*—Morgan & Finnegan

[57] ABSTRACT

An improvement in the process for the manufacture of aliphatic phosphonic acid the improvement comprising maintaining the reaction zone volume at about 80 to 95 percent capacity of reactants and/or products by continuously adding diester of aliphatic phosphonic acid reactant up to about 60 percent of the total reaction time said reactant being added in an amount sufficient such that said reactants and/or products will always be present in said reactor so as to occupy at least 80 percent of the reaction zone volume during said reactant addition.

19 Claims, 6 Drawing Figures

PROCESS FOR THE PRODUCTION OF ALIPHATIC PHOSPHONIC ACIDS

This is a continuation of co-pending application Ser. No. 789,025 filed Oct. 18, 1985, abandoned.

BACKGROUND OF THE INVENTION

1. Field of the Invention

This invention relates to an improved process for the manufacture of aliphatic phosphonic acids, and more particularly to a process for the manufacture of a 2-haloethylphosphonic acid and still more particularly, to the manufacture of 2-chloroethylphosphonic acid.

2. Summary of Prior Art

It is known in the art, that certain aliphatic phosphonic acids, particularly 2-haloethylphosphonic acids and derivatives thereof, are valuable as plant growth regulators in the agricultural field. The chloro compound i.e., 2-chloroethylphosphonic acid has been used extensively as a plant growth regulator for increasing crop yield of, for example, pineapples, soybeans, and the like. The usefulness of these compounds is illustrated for example in the publication of Nature, vol 218, page 974 (1969) by Cooke and Randall; and U.S. Pat. No. 3,879,188 issued Apr. 22, 1985 entitled "Growth Regulation Process" invented by Fritz, Evans, and Cooke.

The manufacture of 2-chloroethylphosphonic acid (ETHEPHON) is well known in the art. British Pat. No. 1,373,513 describes a process for the manufacture of chloroethylphosphonic acid which comprises cleaving the diester with aqueous hydrochloric acid optionally in the presence of gaseous hydrogen chloride at a temperature of about 100° C. and under an elevated pressure, continuously or discontinuously distilling off the 1,2-dichloroethane formed during the reaction and maintaining an elevated pressure by adding gaseous hydrogen chloride continuously or discontinuously during the reaction.

Another variation on the process of cleaving the diester is described in U.S. Pat. No. 3,808,265 which describes a process for the manufacture of 2-chloroethylphosphonic acid by reacting the diester and concentrated aqueous hydrochloric acid under pressure of injected hydrogen chloride gas sufficient to replenish the reacted HCl and maintain the concentration of the aqueous hydrochloric acid above about 23% at a temperature of about 100° C. to 145° C., cooling the reaction product to obtain a two-phase liquid system consisting of an aqueous phase containing 2-chloroethylphosphonic acid and an organic phase containing ethylene dichloride, drawing off the ethylene dichloride phase and recovering 2-chloroethylphosphonic acid from the aqueous phase.

All of the above processes involve the acid cleavage of the ester groups from the diester of the phosphonic acid to yield the corresponding phosphonic acid.

This cleavage reaction for the manufacture of phosphonic acid occurs in a stepwise manner. The diester is converted to the half ester which, in turn, is cleaved to the phosphonic acid.

The cleavage of the bis(2-chloroethyl)-2-chloroethylphosphonate (the diester), by known prior art methods utilizing anhydrous HCl, depending upon reaction conditions and concentrations, can produce from 45 to 84% 2-chloroethylphosphonic acid and from 3 to 30% of the mono-2-chloroethyl-2-chloroethylphosphonate (the half ester).

A major impurity in the manufacture of 2-haloethylphosphonic acid is the half ester of the corresponding acid.

It is highly desirable, when applying 2-haloethylphosphonic acid to plants, that the compositions applied be sufficiently free of impurities such as half esters of 2-haloethylphosphonic acids, to avoid the toxic or potentially toxic effects of these impurities on plants. It is thus highly desirable to either remove the half ester from the crude reaction mixture obtained from the cleavage of the diester of the corresponding acid or to obtain within reasonable operating parameters, i.e., time, pressures, concentrations, etc., substantially complete reaction of the diester and half ester to 2-chloroethylphosphonic acid.

Generally, attempts have been made to purify 2-haloethylphosphonic acid manufactured from the prior art processes.

U.S. Pat. No. 3,626,037 describes the extraction with benzene of the monoester of 2-chloroethylphosphonic acid from a reaction mixture containing the monoester and 2-chloroethylphosphonic acid. The disadvantages of using benzene as a commercially practical extracting solvent are that it is highly flammable, acutely toxic to humans, and gives poor phase separation when used as an extracting solvent for the half ester of haloethylphosphonic acid.

British Pat. No. 1,187,002 describes the extraction of the monoester of 2-haloethylphosphonic acid from the crude reaction mixture with a halo-hydrocarbon of from 1 to 8 carbon atoms, such as chlorobenzene, dichlorobenzene, chloroform, tetrachloroethylene, and preferably methylene chloride or ethylene dichloride. The disadvantages of using halo-hydrocarbons as commercially practical extracting solvents are that they are highly toxic to humans and a poor extracting solvent for the purification of 2-haloethylphosphonic acid.

One serious drawback with attempting to obtain the highly pure aliphatic phosphonic acids necessary for commercial use by the addition of an extracting process to the process of manufacturing is that this extracting process involves an additional step with its concomitant increase in cost, both in capital and operating expenses.

More recently, U.S. Pat. No. 4,064,163 describes in detail a process for the manufacture of an aliphatic phosphonic acid, particularly 2-chloroethylphosphonic acid, of the type wherein a diester of the aliphatic phosphonic acid, particularly bis-(2-chloroethyl)-2-chloroethylphosphonate, is reacted with anhydrous hydrogen halide, particularly hydrogen chloride, to produce a reaction product containing the aliphatic phosphonic acid, and the corresponding aliphatic halides, particularly ethylene dichloride.

In general the process provides:

(a) reacting the diester and the anhydrous hydrogen halide at a first temperature of at least 100° C., at a low pressure and for a first period of time to form a first reaction product;

(b) subsequently reacting the first reaction product and the anhydrous hydrogen halide at a second temperature of at least 100° C., at a high pressure, said high pressure higher than said low pressure, for a second period of time to form a second reaction product; and (c) removing the aliphatic halides from at least one reaction product.

The process, disclosed in U.S. Pat. No. 4,064,163 is particularly related to a process for the manufacture of 2-chloroethylphosphonic acid utilizing the diester bis-(2-chloroethyl)-2-chloroethylphosphonate and wherein the anhydrous hydrogen halide is anhydrous hydrogen chloride. In general, the low pressure should be at least 14 psia and the high pressure at least 20 psia. Preferably, the low pressure is from about 14 psia to about 30 psia and the high pressure is from 30 psia to about 50 psia. In addition, the step of reacting the diester and the anhydrous hydrogen halide and the step of subsequently reacting the first reaction product and the anhydrous hydrogen halide are both accomplished at at least 100° C. Preferably, the first and second temperatures are both from about 140° C. to about 160° C. The temperatures should not exceed 200° C. Below 100° C. the reaction kinetics are such as to cause the reaction to proceed too slowly, whereas above 200° C. product and raw material decomposition interferes with the reactions.

Normally, the first period of time in the first step for the manufacture of 2-chloroethylphosphonic acid in the first step is usually at least about 25 hours and preferably from about 25 to about 35 hours. Further, the second period of time in the process for the manufacture of 2-chloroethylphosphonic acid is until the second reaction product contains a required concentration of at least about 80% by weight of 2-chloroethylphosphonic acid. The second period of time in the preferred process for the manufacture of 2-chloroethylphosphonic acid is at least about 10 hours. Preferably, however, the reaction time is from about 10 hours to about 16 hours. Commercially acceptable 2-chloroethylphosphonic acid for most agricultural uses is generally considered to have a minimum concentration of 85% by weight of 2-chloroethylphosphonic acid in the second reaction product. This can usually be accomplished within a second period of time of about 13 hours.

As will be discerned from the above, present techniques for producing aliphatic phosphonic acids and particularly 2-chloroethylphosphonic acids require a considerable amount of time in the order of about 35–50 hours or more to obtain product purity of at least 90%. This is in part mainly attributable to the batch mode of feeding starting materials to the reaction vessel. As a result of the batch mode of feeding of the starting materials, ethylene dichloride which is continuously evolved and discharged from the reaction vessel results in volume shrinkage of the reaction zone during the reaction period. The volume shrinkage is caused by a decrease in density and evolution of ethylene dichloride. At about 98% conversion, the final volume is only about 50% of the original. Thus it will be seen that the reaction vessel is not efficiently utilized for this type reaction.

It is thus an object of this invention to provide a novel process for manufacturing aliphatic phosphonic acids.

Another object of this invention is to provide a process for manufacturing highly pure aliphatic phosphonic acids at a low cost.

Another object of this invention is to provide a novel manufacturing process which is particularly suitable for manufacturing 2-haloethylphosphonic acids, and more particularly 2-chloroethylphosphonic acid.

Still another object of this invention is to provide a novel process which is particularly suitable for manufacturing, 2-haloethylphosphonic acids of highly pure nature under economically reasonable process parameters.

SUMMARY OF THE INVENTION

Figure 1:
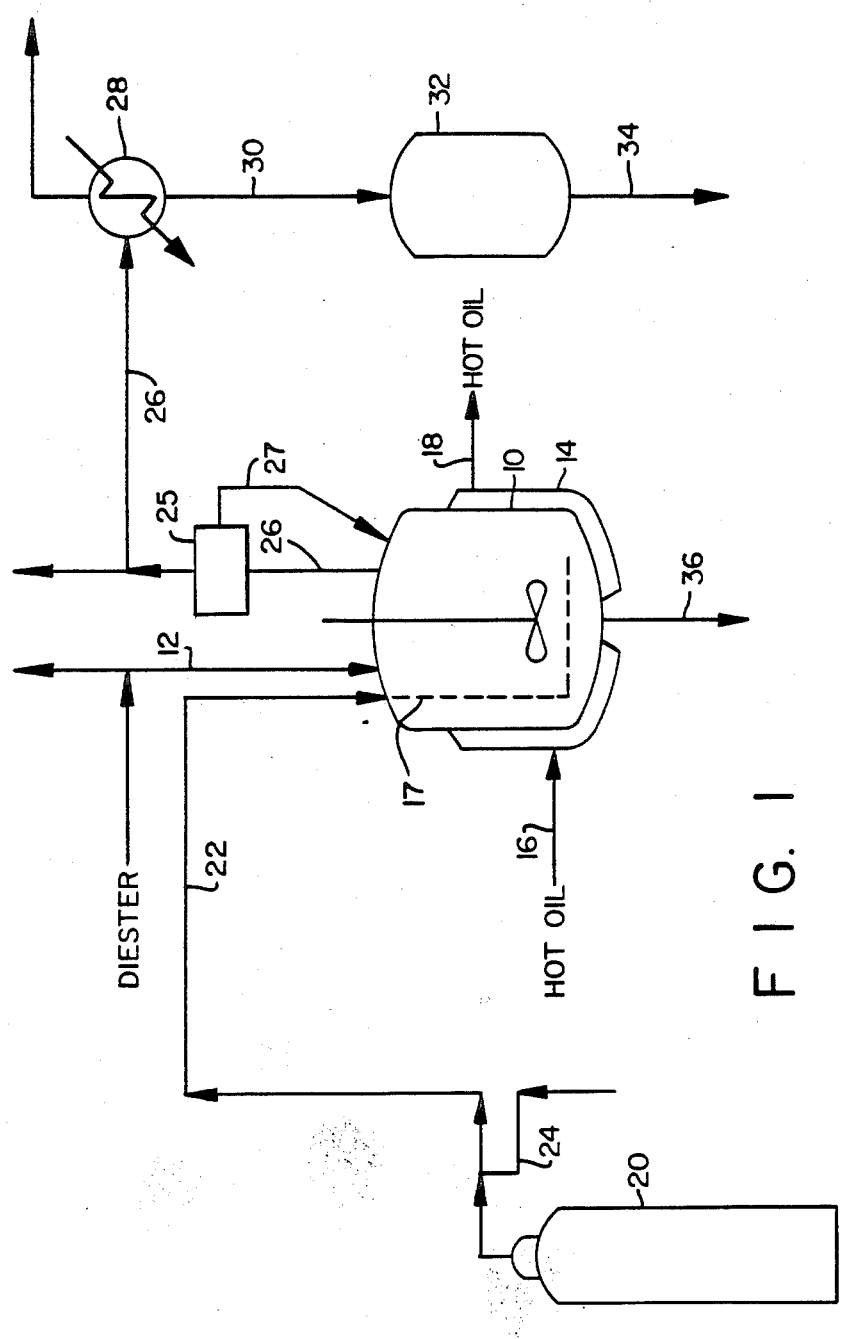
FIG. 1 is a schematic diagram generally illustrating the process for producing 2-chloroethylphosphonic acid.

Broadly contemplated, the present invention provides an improvement in the process for the manufacture of an aliphatic phosphonic acid of the formula:

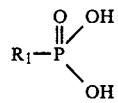

of the type wherein a diester of the aliphatic phosphonic acid of the general formula:

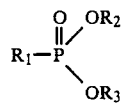

is introduced into a reaction zone with anhydrous hydrogen halide selected from the group consisting of hydrogen chloride, hydrogen bromide, hydrogen iodide and hydrogen fluoride to produce a reaction product containing the corresponding aliphatic phosphonic acid and the corresponding aliphatic halides, wherein $R_1$, $R_2$ and $R_3$ are each independently selected from the group consisting of substituted and unsubstituted aryl, alkyl, alkenyl, halo-substituted alkyl and halo-substituted alkenyl, having from 1 to 6 carbon atoms, and wherein the diester and the anhydrous hydrogen halide are reacted for a first period of time to form a first reaction product; and subsequently reacting the first reaction product and the anhydrous hydrogen halide for a second period of time to form at least about 90% of a second reaction product; the sum of said first period of time and second period of time constituting the total reaction time and wherein aliphatic halides are continuously discharged from at least one reaction product resulting in a decrease in volume of the reaction zone, the improvement comprising continuously adding additional diester of aliphatic phosphonic acid reactant up to about 60% of the total reaction time, said reactant being added in an amount sufficient such that said reactants and/or products will always be present in said reactor so as to occupy at least 80% of the reaction zone volume during said reactant addition.

Preferably, $R_1$, $R_2$ and $R_3$ are the same substituents. It is more preferable, that $R_1$, $R_2$ and $R_3$ are the halo-substituted alkyl substituents, particularly 2-chloroethyl substituents.

DESCRIPTION OF THE PREFERRED EMBODIMENTS

This invention particularly relates to a process for the manufacture of 2-chloroethylphosphonic acid utilizing the diester bis-(2-chloroethyl)-2-chloroethylphosphonate and wherein the anhydrous hydrogen halide is anhydrous hydrogen chloride.

As used herein the term "alkyl" represents straight or branched chain saturated hydrocarbons.

The term "alkenyl" represents straight or branched chain aliphatic hydrocarbons containing at least one double bond.

The terms "halo-substituted alkyl" and "halo-substituted alkenyl" include alkyl and alkenyl groups having one or more hydrogens replaced by a halogen which can be bonded to the same or different carbon atoms in the alkyl or alkenyl group.

The term "halo," as used herein, includes all four halogens, namely chlorine, bromine, iodine and fluorine.

The term "aryl," as used herin, includes both mono- and polycyclic aryl substituents, such as phenyl, naphthyl and other condensed ring systems.

As only representative examples of the phosphonic acids, or mixtures thereof, which may be produced by the process of this invention, there may be mentioned the following:

1. vinyl phosphonic acid,
2. 1-chloroethylphosphonic acid,
3. 2-chloroethylphosphonic acid,
4. 1-chloropropylphosphonic acid,
5. 2-chloropropylphosphonic acid,
6. 2-chlorobutylphosphonic acid,
7. methylphosphonic acid,
8. ethylphosphonic acid,
9. propylphosphonic acid, and
10. butylphosphonic acid.

As indicated previously this process is particularly designed for the manufacture of 2-chloroethylphosphonic acid, a valuable plant growth regulator used in the agricultural field, however, this invention contemplates a process for the manufacture of any of the aliphatic phosphonic acids encompassed by the general formula above and the use of any of the diesters of the aliphatic phosphonic acid encompassed by the general formula above.

The preferred aliphatic phosphonic acid, 2-chloroethylphosphonic acid, is manufactured by utilizing the diester, bis-(2-chloroethyl)-2-chloroethylphosphonate and, preferably, anhydrous hydrogen chloride. The aliphatic halide produced by this reaction is ethylene dichloride.

However, as noted above 2-chloroethylphosphonic acid may also be manufactured by any of the other anhydrous hydrogen halides. Another preferred anhydrous hydrogen halide is anhydrous hydrogen bromide.

Further, this invention envisions the manufacture of 2-chloroethylphosphonic acid from other diesters, wherein $R_1$ is the 2-chloroethyl substituent.

The general reaction mechanism for producing aliphatic phosphonic acids is described in U.S. Pat. No. 4,064,163 and the production of a representative phosphonic acid, i.e., 2-chloroethylphosphonic acid is illustrated below:

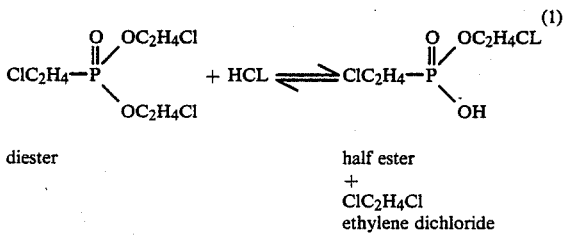

diester        half ester
                    +
                    ClC₂H₄Cl
                    ethylene dichloride

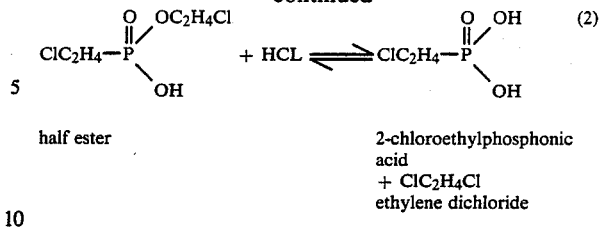

half ester        2-chloroethylphosphonic acid
                          +  ClC₂H₄Cl
                          ethylene dichloride As will be seen from the above, the overall reaction involves a two-step, consecutive, gas-liquid reaction. In general, the reaction is conducted in a reactor equipped with a stirrer or agitator.

The step of (a) reacting the diester and the anhydrous hydrogen halide and the step of (b) subsequently reacting the first reaction product and the anhydrous hydrogen halide in the reactor are both accomplished at at least 100° C. Preferably, the first and second temperatures are both from about 150° C. to about 160° C. The temperatures should not exceed 200° C. Below 100° C. the reaction kinetics are such as to cause the reaction to proceed too slowly, whereas above 200° C. product and raw material decomposition interferes with the reactions.

The total pressure within the reactor can be generally in the order of about 15 to 150 psig. It has been found however that the pressures which are preferred are those within the range of about 40–100 psig.

For reactors equipped with agitating means, the agitator tip speed is preferably about 500–1000 ft./min.

According to the present invention, the process is generally conducted as follows: A conventional reactor, equipped with heating means and agitating or stirring means is filled with liquid phosphonate of the type previously described to about 80% of the working volume of the reactor. The liquid phosphonate is then heated to the required temperature about 120°–180° C., preferably about 150°–160° C. Anhydrous gaseous hydrogen halide is then sparged through the liquid phosphonate at the required pressures which are maintained throughout the reaction. Generally, the gaseous hydrogen halide flow rate is about 2 to 3 times the stoichiometric need. Under the conventional procedure, as the reaction proceeds, the reaction mass shrinks due to evolution of aliphatic halide which is discharged from the reactor at a yield of product of about 95%. During production of the product the decrease in volume in the reactor is about 50% of the original volume. According to the present invention however, this volume shrinkage phenomenon is utilized to increase the production of the final product. Thus, as the volume in the reactor decreases as explained previously, additional phosphonate reactant is added to the reaction zone. In order to obtain maximum gain in reactor productivity, the amount of phosphonate to be added, the starting time and ending time of phosphonate addition are carefully monitored in order to obtain a maximum gain in product reactivity. It has been found that maximum gain in reactor productivity is attained if the additional phosphonate is added up to about 60% and preferably during the first 50–60% of the total reaction time. Merely as illustrative, if the total reaction time is about 10 hours, the additional phosphonate should be charged to the reactor during about 5–6 hours after the reaction has started when conducting the reaction, at the preferred temperatures, pressure, agitator speed and gaseous hydrogen halide flowrate. Generally, the gaseous hydrogen halide sparging is maintained throughout the reaction period with a large excess being used to strip out the aliphatic halide by-product which is discharged from the reactor together with gaseous hydrogen halide and directed to and through a condenser where the liquid aliphatic halide is collected in a condenser accumulator and the non-condensible gaseous hydrogen halide is reacted and neutralized with aqueous rhodium hydroxide.

However, for large scale production, the gaseous hydrogen halide can be compressed for recycle and reuse.

The manner of introducing the additional liquid phosphonate after the initial charge is in a continuous mode. Thus, benefits from practice of the invention can be achieved when the liquid phosphonate is added continuously up to about the first 60% of the total reaction time.

For a more detailed description of the invention and with specific reference to the production of 2-chloroethylphosphonic acid, reference is made to FIG. 1 which shows a schematic diagram of the preferred equipment setup for a 1-gallon glass-lined reactor. It should be understood however, that the major features of the setup are applicable to any size of reactor. Therefore, the process of producing 2-chloroethylphosphonic acid (ETHEPHON) in the 2-liter or 1-gallon reactor will be essentially similar to a much larger reactor, except as mentioned previously, the unreacted HCl will be compressed for recycle and reuse.

According to the process, the reactor 10, is filled with liquid bis(2-chloroethyl-2-chloroethyl)phosphonate entering through line 12 to about 80% of the working volume of the reactor. The reactor is then heated to the preferred temperature of about 150°-160° C. by means of hot oil entering heater jacket 14 through line 16. The hot oil circulates through heater jacket 14 and leaves heater jacket 14 through line 18.

Gaseous hydrogen chloride which is stored in pressurized cylinder 20 is then introduced into reactor 10 through line 22 after it has been purged and blanketed with nitrogen gas fed into line 22, through line 24. The hydrogen chloride is then sparged through the liquid phosphonate as shown by the line 17 at the preferred pressure of approximately 40-100 psig which pressure is maintained throughout the whole reaction period.

In the conventional mode of operation, as the reaction proceeds, the reaction mass shrinks. The shrinkage is about 50% of the original volume at approximately 95% yield.

According to the present invention, however, and when continuous feed of phosphonate is practiced, additional phosphonate is continuously fed to reactor 10 through line 12 and such feeding is continued up to about 50-60% of the total reaction time.

As is known, the by-product in the reaction is ethylene dichloride. The large excess of gaseous hydrochloric acid is utilized to strip out the ethylene dichloride by-product to obtain the maximum space in the reactor for additional phosphonate needed for higher productivity.

Thus, ethylene dichloride vapor and gaseous hydrogen chloride is continuously discharged from reactor 10 through line 26 and passed through gas-liquid separator 25 wherein liquids entrained in or condensed from the ethylene dichloride are returned to reactor 10 through lne 27. The ethylene dichloride and hydrogen chloride thereafter enters condenser 28. In condenser 28, liquid ethylene dichloride is formed and is discharged from condenser 28 through line 30 and is introduced into condenser accumulator 32 where it is collected, sampled if necessary, and drained after the test run.

In the operation illustrated in FIG. 1, the non-condensible gaseous hydrogen chloride can be discharged from condenser accumulator 32 through line 34 and neutralized with sodium hydroxide. For large scale production however, the gaseous hydrogen chloride can be compressed and recycled for reuse.

After the total reaction time, the product in reactor 10 is drawn out through line 36 after about a 90-95% product yield.

For each run, the reaction time, the temperature of reaction, the pressure, the hydrogen chloride flow rate, the agitator speed were monitored. Also at a regular interval during the course of the reaction, a small (liquid phase) sample was withdrawn from the reactor to analyze for the mole percent concentrations of the diester (Bis-2-chloroethyl-2-chloroethyl phosphonate), the monoester(2-chloroethyl hydrogen 2-chloroethyl phosphonate), and the acid (2-chloro-ethylphosphonic acid, or ETHEPHON) by methods well known in the art.

EXAMPLES

The following examples are illustrative of this invention and are not to be considered as limiting.

REACTION RATES DETERMINATION EXAMPLES

The first three examples illustrate the effect of operating pressure on the rate of ETHEPHON or acid production at constant temperature (150° C.), hydrogen chloride (HCl) flow rate (1600 ml/min), agitator speed (1000 rpm) in the one-gallon glass-lined reactor, all at a batch feed mode with respect to the diester or phosphonate.

EXAMPLE 1

Operating Pressure=30 psig

Figure 2:
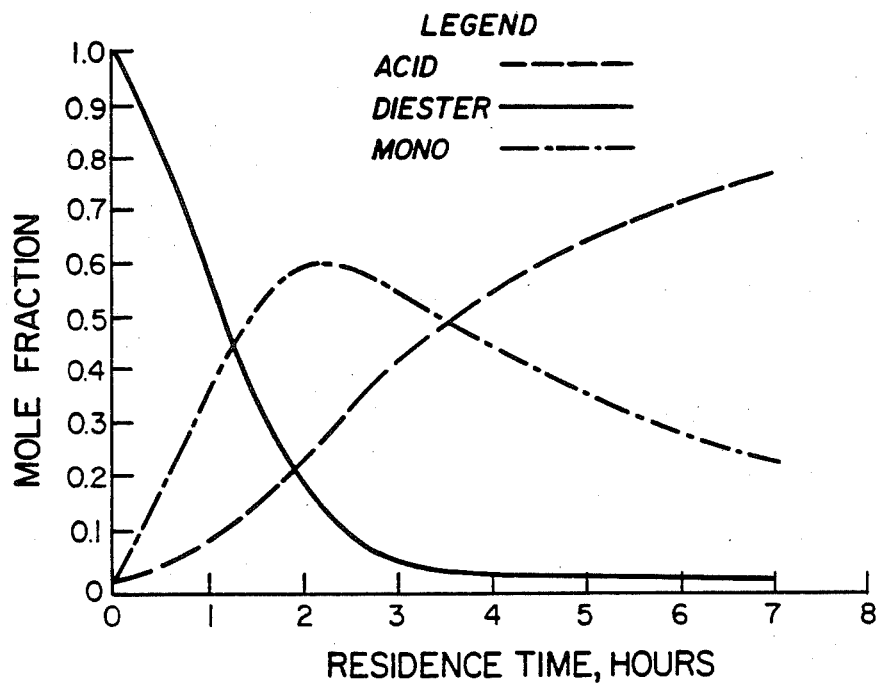
FIGS. 2–6 are graphs generally illustrating mole fraction vs. residence time of ETHEPHON product in reactor under indicated conditions.

This example indicates how the reaction proceeds when the reaction pressure is maintained throughout the reaction at 30 psig. The reaction was run for 7 hours. After 6 hours, Table 1 shows that the acid concentration was 71.7 mole %. The concentration profiles (Mole % vs time) of the reactant and products are shown in FIG. 2.

TABLE 1

| ETHEPHON Reaction: | Batch Reactor Data (1-Gal. Reactor) Temperature = 150° C. Pressure = 30 psig HCl flow - 1600 ml/min RPM = 1000 | |
|---|---|---|
| | Mole % | |
| Time (Hr) | Diester | Mono | Acid |
| 0.0 | 100 | 0.000 | 0.000 |
| 0.5 | 78.9 | 18.5 | 2.5 |
| 1.0 | 56.3 | 36.1 | 7.52 |
| 1.5 | 32.8 | 52.0 | 15.1 |
| 2.0 | 18.3 | 59.1 | 22.5 |
| 2.5 | 8.06 | 58.9 | 33.0 |
| 3.0 | 3.54 | 54.3 | 42.1 |
| 4.0 | 1.25 | 44.2 | 54.5 |
| 5.0 | 0.488 | 34.5 | 65.0 |
| 6.0 | 0.489 | 27.7 | 71.7 |
| 7.0 | 0.277 | 22.0 | 77.6 |

EXAMPLE 2

Operating Pressure=52.5 psig

Figure 3:
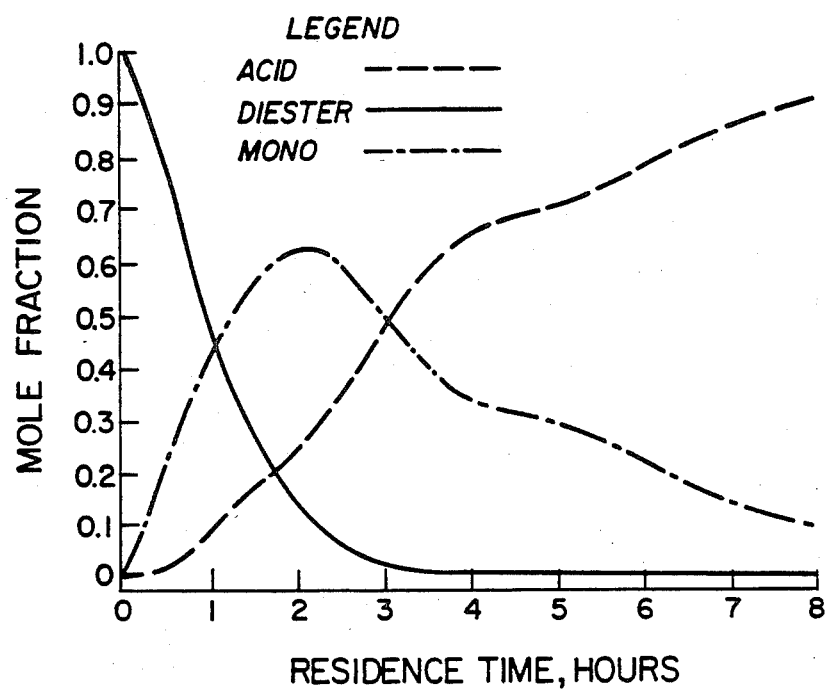

This example shows how the reaction proceeds when the reaction pressure is raised to 52.5 psig. The reaction was run for 8 hours. Table 2 shows that the acid concentration was 78.3% and 91.3% after 6 hours and 8 hours, respectively. The concentration profiles of the reactant and the products are shown in FIG. 3.

TABLE 2

| ETHEPHON Reaction: | Batch Reactor Data (1-Gal. Reactor) Temperature = 150° C. Pressure = 52.5 psig HCl flow = 1600 ml/min. RPM = 1000 | | |
|---|---|---|---|
| Time (Hr) | Diester | Mole % Mono | Acid |
| 0.0 | 100.000 | 0.000 | 0.00 |
| 0.5 | 74.8 | 23.3 | 1.83 |
| 1.0 | 47.1 | 44.1 | 8.68 |
| 1.5 | 27.2 | 55.3 | 17.3 |
| 2.0 | 13.9 | 62.6 | 23.4 |
| 3.0 | 2.16 | 49.6 | 48.2 |
| 4.0 | 0.504 | 33.9 | 65.5 |
| 5.0 | 0.468 | 29.0 | 70.5 |
| 6.0 | 0.232 | 21.4 | 78.3 |
| 7.0 | 0.096 | 13.6 | 86.2 |
| 8.0 | 0.000 | 8.6 | 91.3 |

EXAMPLE 3

Operating Pressure=75 psig

Figure 4:
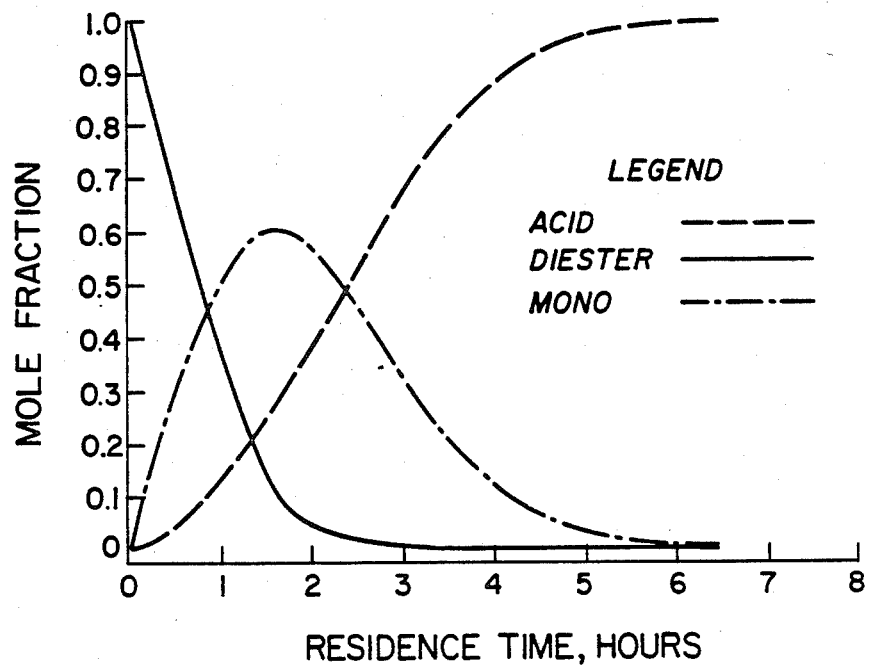

This example illustrates how the reaction proceeds when the reaction pressure is increased further to 75 psig. The reaction was run for 6.5 hours. Table 3 shows that the acid or ETHEPHON concentration was over 99% after 6 hours. The concentration profiles of the reactant and the products are shown in FIG. 4.

TABLE 3

| ETHEPHON Reaction: | Batch Reactor Data (1-Gal. Reactor) Temperature = 150° C. Pressure = 75 psig HCl Flow = 1600 ml/min. RPM = 1000 | | |
|---|---|---|---|
| Time (Hr) | Diester | Mole % Mono | Acid |
| 0.0 | 98.17 | 1.83 | 0.00 |
| 0.5 | 66.46 | 29.68 | 3.83 |
| 1.0 | 36.57 | 49.88 | 13.54 |
| 1.5 | 13.24 | 60.07 | 26.68 |
| 2.0 | 4.65 | 56.56 | 38.78 |
| 3.0 | 0.460 | 31.66 | 67.87 |
| 4.0 | 0.107 | 11.70 | 88.18 |
| 5.0 | 0.068 | 2.91 | 97.01 |
| 6.0 | 0.001 | 0.777 | 99.22 |
| 6.5 | 0.001 | 0.434 | 99.56 |

These first three examples and others like them are used to determine the ETHEPHON synthesis reaction kinetic model. A pseudo-first-order series irreversible reaction model, such as

$$\text{Diester} \xrightarrow{k_1} \text{Monoester} \xrightarrow{k_2} \text{Acid}$$

seems to fit the data very well. The concentration-time profiles of the three main components can then be written as follows:

$$[\text{Diester}]_t = \exp(-k_1 t) \quad (1)$$

$$[\text{Monoester}]_t = \frac{k_1}{k_2 - k_1} [\exp(-k_1 t) - \exp(-k_2 t)] \quad (2)$$

$$[\text{Acid}]_t = 1 - [\text{Diester}]_t - [\text{Monoester}]_t \quad (3)$$

Where in:
$[\text{Acid}]_t$ = the acid or ETHEPHON concentration at time, t, mole fraction.
$[\text{Diester}]_t$ = the diester or phosphonate concentration at time, t, mole fraction.
$[\text{Monoester}]_t$ = the monoester or half ester concentration at time, t, mole fraction.
$k_1$ = the first order (lumped-parameter) rate constant for the conversion of diester to monoester, Hour$^{-1}$
$k_2$ = the first order (lumped-parameter) rate constant for the conversion of monoester to acid, Hour$^{-1}$.
t = reaction time, Hour.

The reaction rate constants, $k_1$ and $k_2$, are correlated as follows:

$$k_1 = \exp(-6.59 - 1.13 \ln(T) + 0.534 \ln(P) + 1.02 \ln(F) + 0.337 \ln(RPM)) \quad (4)$$

$$k_2 = \exp(-20.7 + 2.05 \ln(T) + 0.611 \ln(P) + 0.550 \ln(F) + 0.339 \ln(RPM)) \quad (5)$$

Wherein:
F = HCl flow rate, ml/minute (STP)
P = reaction pressure, psia
RPM = agitator speed, rpm
T = Reaction temperature, °C.
(Only applied in temperature range of 150°–160° C.)

Examples 4–6 illustrate the impact of the manner of introducing the diester or phosphonate on the acid or ETHEPHON productivity, $\phi$, expressed as grams of acid or ETHEPHON produced per (reaction) hour per liter of reactor volume occupied by the diester initially. The reaction conditions for Examples 4–6 are identical:
Reaction temperature, T = 150° C.
Reaction pressure, P = 75 psig
HCl flow rate—1600 ml/minute
Stirring rate = well agitated.

EXAMPLE 4

Batch Phosphonate Feeding Mode

Figure 5:
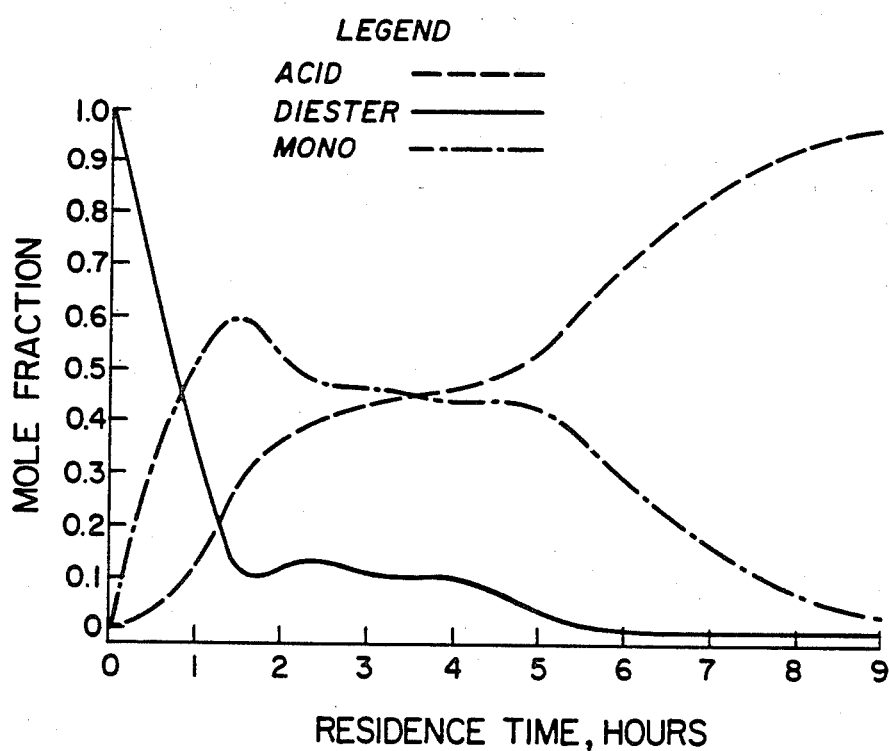

This example will illustrate the production of acid or ETHEPHON the batch phosphonate feeding mode. This is to mean that after a known amount of diester or phosphonate has been charged into the reactor at the beginning of the reaction, no further diester is added throughout the reaction period. Table 4 shows the data obtained (or calculated using the kinetic rate constants previously described), and FIG. 5 depicts the concentration profiles of the diester, monoester and the acid for this example.

TABLE 4

| ETHEPHON Reaction: | Batch Reactor Data (1-Gal. Reactor) Temperature = 150° C. Pressure = 75 psig HCl Flow = 1600 ml/min RPM = 1000 | | | |
|---|---|---|---|---|
| Time (Hr) | Diester | Mole % Mono | Acid | Cumulative Phosphonate Added, mls. |
| 0.0 | 98.170 | 1.830 | 0.000 | 3200 |

TABLE 4-continued

ETHEPHON Reaction: Batch Reactor Data
(1-Gal. Reactor)
Temperature = 150° C.
Pressure = 75 psig
HCl Flow = 1600 ml/min
RPM = 1000

| Time (Hr) | Diester | Mole % Mono | Acid | Cumulative Phosphonate Added, mls. |
|---|---|---|---|---|
| 0.5 | 66.467 | 29.682 | 3.851 | 3200 |
| 1.0 | 36.577 | 49.883 | 13.540 | 3200 |
| 1.5 | 13.241 | 60.077 | 26.682 | 3200 |
| 2.0 | 4.658 | 56.562 | 38.780 | 3200 |
| 3.0 | 0.460 | 31.664 | 67.876 | 3200 |
| 4.0 | 0.107 | 11.706 | 88.187 | 3200 |
| 5.0 | 0.068 | 2.912 | 97.019 | 3200 |
| 6.0 | 0.001 | 0.777 | 99.222 | 3200 |
| 6.5 | 0.001 | 0.434 | 99.566 | 3200 |

From these data, the ETHEPHON productivity, calculated is 123 gms/hr/l. Where $\phi$ is calculated by the following formula:

$$\phi = V_f \times \rho_L \times \frac{(MW)e}{(MW)p} \times [ACID]_f \times \frac{1}{\tau} \times \frac{1}{V_R}$$

wherein:

[Acid]$_f$ = the concentration of acid or ETHEPHON at end of reaction
$V_f$ = the total volume of phosphonate added, ml
$V_R$ = the volume at the beginning of reaction, liters (in 1-gal. reactor VR = 3.785 liters)
$\rho L$ = density of phosphonate, g/ml ($\rho L$ = 1.40)
(MW)e = molecular weight of 2-chloroethylphosphonic acid (ETHEPHON) = 144
(MW)p = molecular weight of bis-(2-chloroethyl)-2-chloroethyl phosphonate(phosphonate) = 269.5
$\tau$ = reaction time, defined as time required to reduce the monoester concentration to equal to or less than 3 (mole) %, hrs. (For example 4, $\tau$ = 5 hrs., monoester concentration is 2.912 mole %, the acid or ETHEPHON concentration is 97.019 mole %.)

EXAMPLE 5

Continuous Phosphonate Feeding Mode

Figure 6:
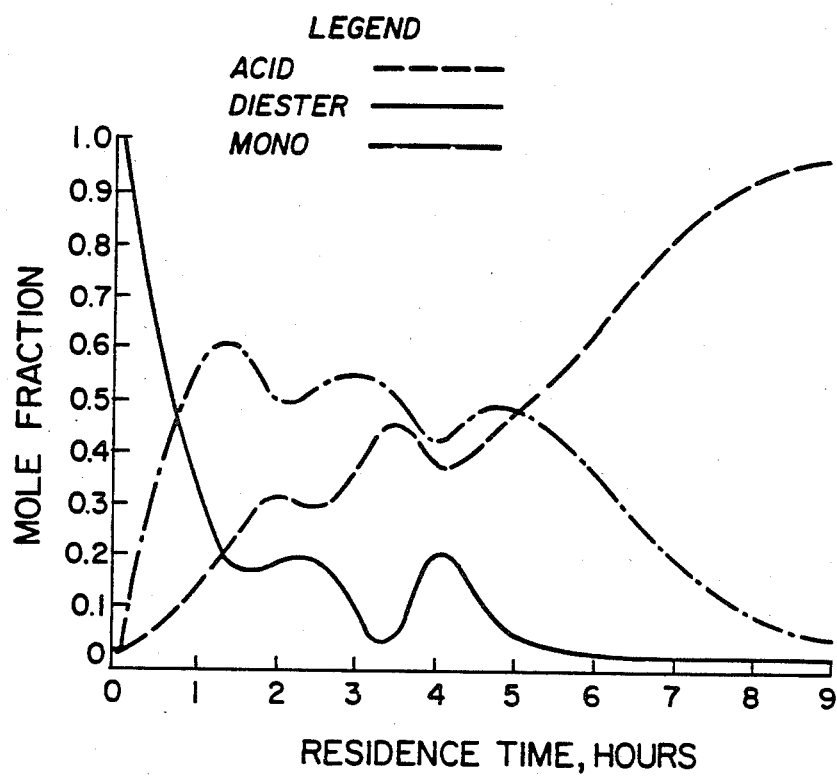

This example illustrates the production of acid or ETHEPHON by the continuous phosphonate or diester feeding mode. In this mode of operation, additional phosphonate is continuously added (by pumping) to the reactor after the initial phophonate charge has been made. As mentioned previously, this is made possible due to the shrinkage in volume as the ethylene dichloride (EDC) formed is immediately stripped out by the excess HCl as the reaction proceeds to completion. Therefore, the addition of phosphonate was guided by the amount of ethylene dichloride collected in the condenser accumulator 32 as shown in FIG. 1. As will be fully explained later, the maximum ETHEPHON productivity is obtained when the addition of phosphonate is continued through approximately the first one-third ($\frac{1}{3}$) of the reaction cycle. Table 5 shows the important data, and FIG. 6 depicts the concentration profiles of the diester, monoester and the acid for this example. From these data, the ETHEPHON "productivity, $\phi$, calculated is 136 gms/hr/l.

TABLE 5

ETHEPHON Reaction: Batch Reactor Data
(1-Gal. Reactor)
Continuous Phosphonate Addition
Temperature = 150° C.
Pressure = 75 psig
HCl Flow = 1600 ml/min
= 1000

| Time (Hr) | Diester | Mole % Mono | Acid | Cumulative Phosphonate Added, mls. |
|---|---|---|---|---|
| 0.0 | 98.529 | 1.471 | 0.000 | 3200 |
| 0.5 | 64.932 | 30.900 | 4.168 | 3200 |
| 1.0 | 34.584 | 52.143 | 13.273 | 3200 |
| 1.5 | 11.469 | 60.048 | 28.484 | 3200 |
| 2.0 | 11.748 | 51.948 | 36.303 | 3780 |
| 3.0 | 10.692 | 46.232 | 43.077 | 4960 |
| 4.0 | 10.191 | 43.705 | 46.103 | 6620 |
| 5.0 | 3.929 | 42.011 | 54.060 | 6620 |
| 6.0 | 0.549 | 28.863 | 70.589 | 6620 |
| 7.0 | 0.109 | 16.097 | 83.794 | 6620 |
| 8.0 | 0.000 | 7.195 | 92.805 | 6620 |
| 9.0 | 0.000 | 3.201 | 96.799 | 6620 |
| 9.3 | 0.000 | 2.88 | 97.09 | 6620 |

EXAMPLE 6

Intermittent Phosphonate Feed Mode

This example illustrates the production of ETHEPHON by the intermittent phosphonate feeding mode (this is a variation of the continuous addition mode in order to increase productivity). In this mode of operation, additional quantity of phosphonate is added at some predetermined elapsed time from the initial phosphonate addition time to bring back the volume of the reaction mass to its initial volume. The amount added would again be guided by the amount of ethylene dichloride collected in the condenser accumulator during the elapsed time. This process can be repeated as many times as desired. The optimum number of additional phosphonate charges and the time interval between additions depends on the operating pressure, temperature, etc. In the present example, two additional phosphonate charges were used: one after 2 hours and the other after 4 hours. The pertinent data are tabulated in Table 6. The ETHEPHON productivity, $\phi$, for this example is calculated to be 133 gms/hr/l.

TABLE 6

ETHEPHON Reaction: Batch Reactor Data
(1-Gal. Reactor)
With Intermittent Phosphonate
Addition Temperature = 150° C.
Pressure = 75 psig
HCl Flow = 1600 ml/min
RPM = 1000

| Time (Hr) | Diester | Mole % Mono | Acid | Cumulative Phosphonate Added, mls. |
|---|---|---|---|---|
| 0.0 | 100.000 | 0.000 | 0.000 | 3200 |
| 1.5 | 16.075 | 60.971 | 22.954 | 3200 |
| 2.0 | 18.289 | 49.634 | 32.077 | 4900 |
| 2.5 | 18.668 | 52.578 | 28.754 | 4900 |
| 3.0 | 8.672 | 54.552 | 36.776 | 4900 |
| 3.5 | 3.844 | 50.420 | 45.736 | 4900 |
| 4.0 | 20.414 | 41.661 | 37.925 | 6600 |
| 4.5 | 12.496 | 47.383 | 40.122 | 6600 |
| 4.8 | 6.488 | 48.570 | 44.943 | 6600 |
| 5.5 | 2.611 | 43.552 | 53.838 | 6600 |
| 6.0 | 0.963 | 36.014 | 63.023 | 6600 |
| 6.5 | 0.300 | 27.028 | 72.672 | 6600 |
| 7.5 | 0.000 | 12.712 | 87.288 | 6600 |
| 8.5 | 0.000 | 5.188 | 94.812 | 6600 |
| 9.0 | 0.000 | 3.854 | 96.146 | 6600 |

TABLE 6-continued

ETHEPHON Reaction: Batch Reactor Data (1-Gal. Reactor) With Intermittent Phosphonate Addition Temperature = 150° C. Pressure = 75 psig HCl Flow = 1600 ml/min
RPM = 1000

| Time (Hr) | Diester | Mole % Mono | Acid | Cumulative Phosphonate Added, mls. |
|---|---|---|---|---|
| 9.5 | 0.000 | 2.55 | 97.42 | 6600 |

It is obvious from examples 4, 5 and 6 that either the continuous mode or the intermittent mode of phosphate addition gives a higher ETHEPHON productivity than the purely batch mode. However, it is time-consuming to determine experimentally the maximum ETHEPHON productivity for both the continuous mode and the intermittent mode of feeding the phosphonate. Thus, a computer program was written to simulate the ETHEPHON synthesis reactions.

After ensuring the validity of the computer model with experimental results, a series of calculations were carried out using this computer model to determine the relative merits of the three different modes of adding phosphonate to the reactor as well as to optimize each mode of phosphonate addition in order to maximize the ETHEPHON productivity for a given size of reactor. Fixed values for the rate coefficient for the two reaction steps ($k_1$ and $k_2$) of 1.10 and 0.55 reciprocal hours, respectively, were used. These were calculated from Equations (4) and (5), respectively, using the same operating conditions as given for Examples 4, 5 and 6, i.e., temperature of 150° C., pressure of 75 psig, HCl flow rate of 1600 ml/hr., and the agitator speed of 1000 rpm. In determining the ETHEPHON productivity, $\phi$, of each operating or phosphonate addition scheme, it was assumed that:

(1) When phosphonate is added, it is added to the original reactor volume occupied by the initial phosphonate charge (which is assumed to occupy 80–85% of the total reactor's working volume).

(2) The reaction is completed when the monoester concentration drops to 0.03 mole fraction.

On these bases, the ETHEPHON productivity, $\phi$, was calculated in grams of ETHEPHON produced per working volume. The results are tabulated in Table 7.

TABLE 7

COMPARATIVE ETHEPHON PRODUCTIVITY

| Case | Mode | Phosphonate Addition Scheme | $\tau$, Total Reaction Time, Hrs. | ETHEPHON Productivity $\phi$, gm/l/hr | Relative ETHEPHON Productivity |
|---|---|---|---|---|---|
| 1 | Batch | Initial charge only | 7.61 | 8.25 | 1.0 |
| 2 | Continuous | Add phosphonate continuously thru end of reaction | 11.2 | 112 | 1.36 |
| 3 | Continuous | Add phosphonate continuously for first 2.8 hrs ($\frac{1}{3}$ of $\tau$) | 8.23 | 122 | 1.48 |
| 4 | Continuous | Add phosphonate continuously for 1st 5.6 hrs (60% of $\tau$) | 9.29 | 125 | 1.52 |
| 5 | Continuous | Add phosphonate continuously for first 8.4 hrs (or 80% of $\tau$) | 10.4 | 118 | 1.43 |
| 6 | Intermittent | One addition of phosphonate at 2.5 hrs after reaction starts | 8.71 | 101 | 1.22 |
| 7 | Intermittent | Two additions of phosphonate at 1.5 and 3.5 hrs after reaction starts | 9.01 | 109 | 1.32 |
| 8 | Intermittent | Three additions of phosphonate at 1.5, 3, and 4.5 hours after reaction starts | 9.4 | 112 | 1.36 |

Examination of Table 7 clearly indicates the following:

(1) The continuous mode of adding phosphonate (after the initial charge) gives the highest ETHEPHON productivity. For example, the best of the continuous mode gives approximately a 50% and a 12% higher $\phi$ than the batch mode and the "best" of the intermittent mode of phosphonate addition, respectively. In the continuous mode of operation, even though the overall reaction time is greater, the reactor volume is more fully utilized to convert phosphonate to ETHEPHON to yield a higher ETHEPHON productivity.

(2) Within the continuous mode of operation, it is better (yielding the highest $\phi$) to continuously add phosphonate through only the first 60% of the reaction time, rather than through the total reaction time. This is because the second reaction, i.e., the conversion of monoester to ETHEPHON, is slower than the first reaction—the conversion of phosphonate to monoester. Therefore, the phosphonate added in the latter part of the reaction cycle takes proportionally a longer time to be converted to ETHEPHON, thereby lowering the $\phi$, the ETHEPHON productivity.

(3) Within the intermittent mode of operation, it is better (yielding higher $\phi$) to have more phosphonate additions. Again, the reason is that the higher the frequency of addition, the quicker it approaches the continuous mode of operation.

What is claimed is:

1. In the process for the manufacture of an aliphatic phosphonic acid of the formula:

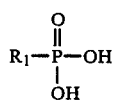

of the type wherein a diester of the aliphatic phosphonic acid of the general formula:

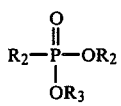

is introduced into a reaction vessel as a liquid phase and reacted with a flow of anhydrous hydrogen halide selected from the group consisting of hydrogen chloride, hydrogen bromide, hydrogen iodide and hydrogen fluoride to produce a reaction product containing the corresponding aliphatic phosphonic acid and the corresponding aliphatic halides, wherein $R^1$, $R_2$ and $R_3$ are each independently selected from the group consisting of substituted and unsubstituted aryl, alkyl, alkenyl, halosubstituted alkyl and halosubstituted alkenyl, having from 1 to 6 carbon atoms, and wherein the diester and the anhydrous hydrogen halide are reacted at a temperature of at least about 100° C., a pressure of about 30 psig to 150 psig with vigorous agitation, for a first period of time to form a first reaction product; and subsequently reacting the first reaction product and the anhydrous hydrogen halide for a second period of time to form at least about 90 percent of the aliphatic phosphonic acid; the sum of said first period of time and second period of time constituting the total reaction time and wherein aliphatic halides are continuously discharged from the reaction vessel, the improvement comprising maintaining the volume of liquid phase in the reaction vessel at about 80 to 95 percent volume capacity of the reaction vessel by continuously adding sufficient amount of the diester of the aliphatic phosphonic acid reactant during the first about 50 to 60 percent of the total reaction time.

2. The process of claim 1, wherein $R_1$, $R_2$, and $R_3$ are the same.

3. The process of claim 1, wherein $R_1$, $R_2$, and $R_3$ are the same halo-substituted alkyl.

4. The process of claim 1, wherein the aliphatic phosphonic acid is 2-chloroethylphosphonic acid.

5. The process of claim 4, wherein the diester is bis(2-chloroethyl)-2-chloroethyl phosphonate.

6. The process of claim 1, wherein the anhydrous hydrogen halide is anhydrous hydrogen chloride.

7. The process of claim 6, wherein the aliphatic halides are ethylene dichloride.

8. The process of claim 1, wherein:
   (a) The aliphatic phosphonic acid is 2-chloroethylphosphonic acid;
   (b) The diester is bis(2-chloroethyl)-2-chloroethyl phosphonate;
   (c) The anhydrous hydrogen halide is anhydrous chloride; and
   (d) The aliphatic halides are ethylene dichloride.

9. A process according to claim 1 wherein said aliphatic halides removed from said reaction vessel is passed through gas-liquid separation means and liquids entrained in or condensed from said aliphatic halide is returned to said reaction vessel.

10. A process according to claim 1 wherein said additional diester of aliphatic phosphonic acid reactant is continuously added about 60 percent of the total reaction time.

11. A process according to claim 1 wherein the flow rate of said anhydrous hydrogen halide is about 2 to 3 times the stoichiometric need.

12. A process according to claim 1 wherein the temperature within said reactor is at least about 150° C. to about 160° C.

13. A process according to claim 1 wherein the total pressure in the reaction zone is about 50 to about 100 psig.

14. A process for the production of 2-chloroethyl phosphonic acid with comprises:
   (a) introducing anhydrous hydrochloric acid and bis 2-chloroethyl ester of 2-chloroethyl phosphonic acid into a reaction vessel in amounts sufficient that about 80 percent by volume of said reaction vessel is occupied by liquid phase at a temperature of at least about 100° C. and a pressure of about 30 psig to 150 psig with vigorous stirring such that said ester will undergo a two-stage saponification reaction with anhydrous hydrochloric acid to product the desired product, 2-chloroethyl phosphonic acid and dichloroethylene as the principal byproduct;
   (b) continuously removing said dichloroethylene from said reaction vessel; and
   (c) continuously adding during the first about 50 to 60 percent of the total reaction time, sufficient amounts of said ester to said reaction vessel to maintain the total volume of the liquid phase within said reaction vessel at a level of at least about 80 percent of the total volume of said reaction vessel during said continuous addition of said ester.

15. A process according to claim 14 wherein said dichloroethylene removed from said reaction vessel is passed through gas-liquid separation means and liquids entrained in or condensed from said ethylene dichloride are returned to the said reaction vessel.

16. A process according to claim 14 wherein said additional amounts of said ester is continuously added to about 60 percent of the total reaction time.

17. A process according to claim 14 wherein the flow rate of said anhydrous hydrochloric acid is about 2 to 3 times the stoichiometric need.

18. A process according to claim 14 wherein the temperatures within said reaction zone is at least about 150° C. to about 160° C.

19. A process according to claim 14 wherein the total pressure in the reaction zone is about 50 to about 100 psig.

* * * * *

UNITED STATES PATENT AND TRADEMARK OFFICE
CERTIFICATE OF CORRECTION

PATENT NO. : 4,728,466

DATED : March 1, 1988

INVENTOR(S) : Kai W. Young and John J. Zullo

It is certified that error appears in the above-identified patent and that said Letters Patent is hereby corrected as shown below:

In the Specification

Column 2, line 31: Delete "British Patent No. 1,187,002" and insert therefor -- U.S. Patent 4,293,505--.

Signed and Sealed this

Seventh Day of August, 1990

Attest:

HARRY F. MANBECK, JR.

Attesting Officer

Commissioner of Patents and Trademarks